United States Patent [19]

Cahoy et al.

[11] Patent Number: 5,280,008

[45] Date of Patent: Jan. 18, 1994

[54] DRY, WATER-SOLUBLE POWDER, SUBSTITUTED HETEROCYCLIC ACID OR SUBSTITUTED PHENOL HERBICIDAL COMPOSITIONS, AND METHOD OF PREPARING SAME

[75] Inventors: Roger P. Cahoy, Overland Park; John L. Van Haften, Leawood, both of Kans.

[73] Assignee: PBI-Gordon Corporation, Kansas City, Mo.

[21] Appl. No.: 76,453

[22] Filed: Jun. 14, 1993

Related U.S. Application Data

[63] Continuation-in-part of Ser. No. 745,866, Aug. 16, 1991, Pat. No. 5,221,319, and a continuation-in-part of Ser. No. 911,757, Jul. 10, 1992, abandoned, and a continuation-in-part of Ser. No. 928,132, Aug. 10, 1992.

[51] Int. Cl.$^5$ .............................................. A01N 25/12
[52] U.S. Cl. ................................. 504/116; 504/130; 504/131; 504/141; 504/222; 504/244; 504/247; 504/254; 504/260; 504/310
[58] Field of Search ............... 504/116, 130, 131, 141, 504/222, 244, 247, 254, 260, 310

[56] References Cited

U.S. PATENT DOCUMENTS

| | | | |
|---|---|---|---|
| 4,015,970 | 4/1977 | Hennart | 71/11 |
| 4,332,614 | 6/1982 | Alt | 71/118 |
| 5,022,182 | 6/1991 | Anderson | 47/48.5 |
| 5,022,917 | 6/1991 | Allan | 71/DIG. 1 |
| 5,160,528 | 11/1992 | Chaudhuri et al. | 71/79 |

OTHER PUBLICATIONS

The Chemistry of OPen-Chain Organic Nitrogen Compounds, vol. I, P. A. S. Smith, pp. 267-269 (1965).
Advances in Pesticide Formulation Technology, ACS Symposium Series 254, Paper 14, "Steps of Water Dispersible Granule Development", Wright and Ibrahim, pp. 185-192 (1984).
Pesticide Formulations, Innovations and Developments, ACS Symposium Series 371, Chapter 20, "Development of Solid Pesticide Formulations of Fluidized-Bed Technology", Lin, pp. 251-259 (1988).

*Primary Examiner*—Richard L. Raymond
*Assistant Examiner*—S. Mark Clardy
*Attorney, Agent, or Firm*—Hovey, Williams, Timmons & Collins

[57] ABSTRACT

Dry, water-soluble powder, substituted heterocyclic acid, substituted phenol herbicidal compositions, combinations thereof, or in combination with phenoxy and/or benzoic acid herbicides, are prepared by grinding and dry blending the herbicide in acid form with a dry, particulate solubilization medium selected from the group consisting of diammonium phosphate, dipotassium phosphate, disodium phosphate, trisodium phosphate or tripotassium phosphate. At least about 1 mole of the medium is provided for each mole of active herbicidal agent in the initially dry blended mixture. The dry blended mixture may be packaged in suitable containers such as paper bags, and added directly to a quantity of water to form a solubilized herbicidal formulation containing from about 0.1% to about 2-½% of the active herbicide and which is suitable for direct application to vegetation to be controlled.

36 Claims, No Drawings

DRY, WATER-SOLUBLE POWDER, SUBSTITUTED HETEROCYCLIC ACID OR SUBSTITUTED PHENOL HERBICIDAL COMPOSITIONS, AND METHOD OF PREPARING SAME

RELATED APPLICATIONS

This application is a continuation-in-part of application Ser. No. 07/745,866, filed Aug. 16, 1991, now U.S. Letters Pat. No. 5,221,319; application Ser. No. 07/911,757, filed Jul. 10, 1992, which is now abandoned; and pending application Ser. No. 07/928,132, filed Aug. 10, 1992.

BACKGROUND OF THE INVENTION

1. Field of the Invention

This invention relates to water-soluble herbicidal compositions in dry powdered form which include herbicidally active agents selected from the group consisting of a herbicidally active substituted heterocyclic acid, a herbicidally active substituted heterocyclic acid combined with a solid herbicidally active substituted phenoxy acid, a herbicidally active substituted heterocyclic acid combined with a solid herbicidally active substituted benzoic acid, a herbicidally active substituted heterocyclic acid combined with a herbicidally active substituted phenoxy acid and a herbicidally active substituted benzoic acid, and a herbicidally active substituted phenol, each of which alone, or in combination with one another, are not readily soluble in water.

2. Description of the Prior Art

Those herbicidal agents registered for use by commercial applicators are generally sold in concentrated form for economy of transport, and then diluted by the applicator either at a central distribution center, or less frequently at the point of use. The majority of effective herbicides and plant growth regulators are foliarly absorbed and therefore, to be effective, must be applied to the foliage of the target pest species. Other herbicides are root absorbed and the product must be applied in a manner as to be available to the roots of the target. This is commonly accomplished by spraying a dilute water solution, or dispersion of the desired pesticide on the vegetation to be treated. Most herbicides are therefore marketed as either (1) liquid or dry water-soluble formulations, (2) liquid, water emulsifiable formulations, or (3) solid or liquid water dispersible formulations. The concentrated formulations are diluted to the required effective concentration by the person doing the spray application. Thus, in order to obtain optimum effectiveness and to minimize agitation and other mechanical suspension requirements, water-soluble formulations are normally preferred.

Because of the difficulties of manufacturing a dry, soluble form of herbicide, most dry formulations are simply dispersible forms of essentially insoluble active ingredients. Typical examples of formulations are (1) wettable powders, (2) water dispersible granules, or (3) dry flowables. Formulations of these types depend heavily on surfactants and grinding techniques to provide a dry formulation of active ingredients that can be temporarily dispersed or suspended in water for spray application. Even when a dispersion can initially be obtained in water, the time of full dispersion is usually limited, thus requiring stirring, agitation with air, or other mechanical mixing. Dispersions of this type present additional problems in that the material tends to clog spray nozzles and other distribution components, and require the user to prepare smaller than desired batches in order to minimize application problems.

Because of the problems associated with attempting to prepare the dry powdered herbicide, suppliers have resorted in some instances to dissolution of the active ingredient in an organic solvent such as mineral spirits or the like. The concentrated formulation, containing suitable surfactants, is then diluted with water to form a dispersion that again usually necessitates some type of agitation to maintain the phases substantially homogeneous for a useful period of time.

In instances where the herbicides are dissolved in a solvent for shipment as a concentrate, the solvent presents health and physical hazards to the manufacturer as well as the user, the solvents add to the overall cost of the product, and the solvent agent is oftentimes phytotoxic to desirable plant species.

The wettable powders and solvent dissolved herbicides are frequently packaged in plastic containers and disposal of these plastic packages is becoming increasingly difficult from an environmental standpoint.

Substituted phenoxy and/or benzoic acid herbicides such as (2,4-dichlorophenoxy)acetic acid [2,4-D], 4-(2,4-dichlorophenoxy)butanoic acid [2,4-DB], (+)-2-(4-chloro-2-methylphenoxy)propanoic acid [MCPP], (4-chloro-2-methylphenoxy)acetic acid [MCPA], (+)-2-(2,4-dichlorophenoxy)propanoic acid [dichlorprop], 3,6-dichloro-2-methoxybenzoic acid [dicamba], 3-amino-2,5-dichlorobenzoic acid [chloramben], and 5-[2-chloro-4-(trifluoromethyl)phenoxy]-2-nitrobenzoic acid [acifluorfen] have long been used to control unwanted vegetation.

These substituted phenoxy and/or benzoic acid herbicides are white crystalline solids with very low vapor pressures and low water solubilities. They are soluble only in alkaline solutions or polar organic solvents.

Phenoxy and/or benzoic acid herbicides are available commercially as acid, ester, alkali metal, and amine salt formulations that can also be applied as mixtures with other herbicides. The alkali metal and especially the amine salt formulations are preferred because they are the most water-soluble and can be more readily applied as aqueous sprays. However, the esters must be applied either as emulsions in water, or as solutions in organic solvents such as oils. 2,4-D for example, is an insoluble crystalline material having a $pK_a$ of approximately 2.6. For ease of application, 2,4-D is normally converted to a water-soluble amine or mineral salt by the manufacturer and then dissolved by the applicator in a water carrier before use.

However, water-soluble substituted phenoxy and/or benzoic acid salts exhibiting herbicidal activity are difficult to prepare in a dry state. Soluble salts such as potassium or sodium or dimethylamine must be first prepared in water or a solvent and then the solvent removed. This requires special equipment, is energy intensive, and frequently generates undesirable waste products. As a consequence, most dry forms of herbicide that are marketed are not of a soluble type but rather are merely dispersible forms of the essentially insoluble herbicide acid which are distributed as a wettable powder or a wettable, dispersible granule. Although both inorganic and organic salt forms are commercially available, the most common salt form is the dimethylamine salt of the substituted phenoxy or substituted benzoic acid herbicide. Typical formulations range from about 20% to 50% active ingredient concentrations in water or solvent solutions.

Similarly, 3,6-dichloropicolinic acid as a monoethanolamine salt [clopyralid], 3,5,6-trichloro-2-pyridyloxyacetic acid as a triethylamine salt [triclopyr], 4-amino-3,5,6-trichloropicolinic acid as a potassium salt [picloram], 3,7-dichloro-8-quinolinecarboxylic acid as a 50% wettable powder [quinclorac] and 3-isopropyl-1H-2,1,3-benzothiadiazin-4 (3H)-one 2,2-dioxide as a sodium salt [bentazon] have been used commercially as herbicidal compositions.

Picloram has been combined with the amine salt of 2,4-D acid, clopyralid has been combined with the amine salt of 2,4-D acid, and triclopyr plus 2,4-D acid as an EC ester, have all been suggested and are in use as herbicidal agents.

Wettable powders, water-soluble amine salts, oil soluble amine salts, and emulsifiable concentrates have 10 also been provided of substituted phenolic herbicides including a 33.4% octanoic acid ester of 3,5-dibromo-4-hydroxybenzonitrile [bromoxynil], a 31.7% octanoic acid ester of bromoxynil plus 34% of isooctyl ester of 2-methyl-chlorophenoxyacetic acid, bromoxynil plus MCPA, and the octanoic acid ester of 3, 5-diiodo-4-hydroxybenzonitrile [ioxynil]. Various combinations of ioxynil and/or bromoxynil have been marketed in various foreign countries.

The water solubility of a solid herbicidal phenol such as bromoxynil is no more than about 130 mg/L. The water solubility of ioxynil is no greater than about 50 mg/L.

All of these herbicidal compositions suffer from the disadvantage that the acids either have to be converted to water-soluble form by forming amine salts therefrom, or other equivalent treatment, before they may be used by an applicator.

SUMMARY OF THE INVENTION

The present invention relates to a method of preparing dry, water-soluble powder, substituted heterocyclic acid or substituted phenol herbicidal compositions. The invention also concerns dry, water-soluble, powder, substituted heterocyclic acid or substituted phenol herbicidal compositions which may be dissolved in water at concentrations providing from at least about 0.1% to at least about 2-½% by weight of the active herbicide in the final herbicidal solution.

A dry herbicidal product is preferred over a liquid concentrated herbicide for a number of reasons. Dry formulations are more stable to temperature variations encountered in storage and shipping. For example, freezing can destabilize liquid products interfering with the effectiveness of the herbicide. Similarly, high storage temperatures can lead to solvent losses when an organic solvent is used to dissolve the agent or cause hydrolysis when water is a solvent, thereby adversely affecting active ingredient concentrations.

Dry herbicidal formulations are less dangerous than liquid products. Package leakage during handling is much less likely. If accidentally punctured, dry package leakage is much less severe and easier to clean up than a liquid product. Also, personnel protection is easier to accomplish with dry products because the material cannot as easily splash into the eyes or skin of the applicator. Spills of solvent containing formulations are potentially flammable, further militating against the use of solvents for dissolving the herbicide.

The ease of packaging is significantly enhanced with dry products over liquid formulations and packaging flexibilities are greatly enhanced. Paper containers or wax treated packages can be used, as well as plastic containers. With liquids, specially treated plastic containers or glass containers are normally required. Paper or cardboard packages can be compressed and disposed of much easier than plastic, glass or metal containers.

Transportation costs of dry products are potentially less expensive than is the case where a liquid carrier must also be transported. Although a number of concentrated liquid products having a fairly high active ingredient content are in commercial use, many formulations are sold in the 20-30% active ingredient range with the remainder of the product being water along with a small amount of dispersing agents or product appearance or handling enhancers.

The dry, water-soluble powder, substituted heterocyclic acid or substituted phenol herbicidal compositions of the subject invention are prepared by dry blending the herbicidal agent with a quantity of solid, substantially anhydrous diammonium phosphate (DAP), dipotassium phosphate (DPP), disodium phosphate (DSP), trisodium phosphate (TSP), tripotassium phosphate (TPP), and mixtures thereof which serves as a solubilization medium for the herbicidal agent. A sufficient amount of the DAP, DPP, DSP, TSP or TPP solubilization medium is provided in the dry blended mixture in relationship to the quantity of herbicidal agent combined therewith to cause the dry blended mixture to substantially dissolve in water during preparation of a herbicidal solution which contains an adequate proportion of the herbicidal agent to provide from about 0.1% to about 2-½% by weight of the active herbicide in the herbicidal solution.

A sufficient amount of the DAP, DPP, DSP, TSP or TPP solubilization medium is dry blended with the dry substituted heterocyclic acid or phenolic herbicidal agent, or a heterocyclic acid and phenolic herbicide with a phenoxy or benzoic acid herbicide to provide at least about 1 mole and to about 5 moles of the phosphate medium for each mole of active herbicidal agent in the dry blended mixture.

The dry, water-soluble substituted heterocyclic acid or substituted phenol herbicides are easily manufactured by dry blending the ingredients in powdered form. No unusual manufacturing techniques are required such as grinding to very fine sizes or classification procedures normally necessary to obtain a suitable dispersible product. Product raw material costs are comparable to widely used organic amine or salts of substituted heterocyclic or substituted phenol herbicide formulations currently being marketed. The raw materials are all commercially available and readily obtainable at competitive prices.

DETAILED DESCRIPTION OF THE INVENTION

A quantity of a substantially solid herbicidal agent selected from the group consisting of a herbicidally active substituted heterocyclic acid, a herbicidally active substituted heterocyclic acid combined with a solid herbicidally active substituted phenoxy acid, a herbicidally active substituted heterocyclic acid combined with a solid herbicidally active substituted benzoic acid, a herbicidally active substituted heterocyclic acid combined with a herbicidally active substituted phenoxy acid and a herbicidally active substituted benzoic acid, a herbicidally active substituted phenol, a herbicidally active phenol combined with a herbicidally active substituted heterocyclic acid, a herbicidally active phenol combined with a herbicidally active substituted phenoxy acid, and a herbicidally active phenol combined with a herbicidally active substituted benzoic acid, each of which alone, or in combination with one another, are not readily soluble in water is added to an amount of a substantially solid solubilization medium for the herbicidal agent. The preferred solubilization agent is a quantity of solid, substantially anhydrous diammonium phosphate (DAP), dipotassium phosphate (DPP), disodium phosphate (DSP), trisodium phosphate (TSP), tripotassium phosphate (TPP), and mixtures thereof which serves as a solubilization medium for the herbicidal agent.

Examples of useful substituted heterocyclic herbicides include: 3,6-dichloropicolinic acid [clopyralid]; 3,5,6-trichloro-2-pyridyloxyacetic acid [triclopyr]; 4-amino-3,5,6-trichloropicolinic acid [picloram]; 3,7-dichloro-8-quinolinecarboxylic acid [quinclorac]; and 3-isopropyl-1H-2,1,3-benzothiadiazin-4(3H)-one 2,2-dioxide bentazon]. These single heterocyclic acids may be combined if desired in herbicidally active ratios with substituted phenoxy and/or benzoic acid herbicides which are in the acid form. Examples of useful phenoxy and/or benzoic acid herbicides are (2,4-dichlorophenoxy) acetic acid [2,4-D], 4-(2,4-dichlorophenoxy) butanoic acid [2,4-DB], (±)-2-(4-chloro-2-methylphenoxy)propanoic acid MCPP], (4-chloro-2-methylphenoxy)acetic acid [MCPA], (±)-2-(2,4-dichlorophenoxy)propanoic acid [dichlorprop], 3,6-dichloro-2-methoxy-benzoic acid [dicamba], 3-amino-2,5-dichlorobenzoic acid [chloramben], and 5-[2-chloro-4-(trifluoromethyl)-phenoxy]-2-nitrobenzoic acid [acifluorfen].

The herbicidal compositions therefore may comprise a single herbicidal substituted heterocyclic acid, the combination of a substituted heterocyclic acid with a solid herbicidal substituted benzoic acid, or the combination of a substituted heterocyclic acid with a solid herbicidal substituted phenoxy acid. None of these herbicides, or combinations thereof, are readily soluble in water.

Examples of substituted phenolic herbicides useful in this invention include: 3,5-dibromo-4-hydroxybenzonitrile [bromoxynil]; bromoxynil plus MCPA; and 3,5-diiodo-4-hydroxybenzonitrile [ioxynil]; and combinations of ioxynil and bromoxynil.

Preferred formulations include at least about 25 weight percent of the active herbicidal acid, and in certain instances about 50 weight percent of the active herbicidal agent or combinations thereof.

The herbicidal agent and the phosphate solubilization medium are dry blended to produce a substantially homogeneous mixture thereof. This dry blended mixture may be packaged in paper containers, or other suitable packages, without further processing such as pulverization, extended grinding, or critical classification. However, the particle size is preferably small enough to permit relatively rapid wetting when added to water. At least about 1 mole to about 5 moles of the solubilization medium is provided for each mole of active herbicidal agent in the dry blended mixture.

EXAMPLE I

The following ingredients were dry blended:

| Ingredients | % Active Ingredients | Weight % Reagents | Makeup for Grinding of 15 Grams - In Grams | HPLC (High Performance Liquid Chromatography Analysis) |
| --- | --- | --- | --- | --- |
| 1. Clopyralid acid Tech. Grade - (95%) | 50.00 | 52.63 | 7.89 | 49.92 |
| 2. Sodium napthalenesulfonate formaldehyde polymer (Lomar PW) | | 1.00 | 0.15 | |
| 3. Sorbitan tristearate (SPAN-65) | | 1.00 | 0.15 | |
| 4. Spray dry synthetic silica (Wessalon 50-S) | | 2.00 | 0.30 | |
| 5. DAP - Diammonium Phosphate - Reagent Grade - 98% | | 43.47 | 6.51 | |
| Totals | | 100.00% | 15.00 gms. | |

Ingredients 1-5 of Example I were ground to a fine, dry powder (averaging about 50 microns particle size) in a laboratory analytical mill. The mixture was transferred to a capped glass container. A 2 gm. sample of the 50% active herbicide powder prepared in accordance with Example I was added to a glass graduated cylinder which contained 98 ml. of city water. The stoppered cylinder was inverted several times over a period of 5 minutes. The 2 weight percent of herbicidal agent added to the water dissolved, with only a small quantity of silica remaining as a dispersion. After 96 hours in an oven at 50° C., a sample of the powder indicated no visible changes.

EXAMPLE II

The following ingredients were dry blended:

| Ingredients | % Active Ingredients | Weight % Reagents | Makeup for Grinding of 15 Grams - In Grams | HPLC (High Performance Liquid Chromatography Analysis) |
| --- | --- | --- | --- | --- |
| 1. Triclopyr acid Tech. Grade - (98%) | 50.00 | 51.02 | 7.65 | 50.11 |
| 2. Sodium napthalenesulfonate formaldehyde polymer (Lomar PW) | | 1.00 | 0.15 | |
| 3. Sorbitan tristearate (SPAN-65) | | 1.00 | 0.15 | |
| 4. Spray dry synthetic silica (Wessalon 50-S) | | 5.00 | 0.75 | |
| 5. DAP - Diammonium Phosphate - Reagent Grade - 98% | | 41.98 | 6.30 | |
| TOTALS | | 100.00% | 15.00 gms. | |

The 50% active herbicide powder was prepared in accordance with Example I. Water solubility and oven stability were, likewise, similar.

EXAMPLE III

The following ingredients were dry blended:

| Ingredients | % Active Ingredients | Weight % Reagents | Makeup for Grinding of 15 Grams - In Grams | HPLC (High Performance Liquid Chromatography Analysis) |
|---|---|---|---|---|
| 1. Bentazon acid Tech. Grade - (92.4%) | 50.00 | 54.11 | 5.41 | 52.42 |
| 2. Sodium napthalenesulfonate formaldehyde polymer (Lomar PW) | | 1.00 | 0.10 | |
| 3. Sorbitan tristearate (SPAN-65) | | 1.00 | 0.10 | |
| 4. Spray dry synthetic silica (Wessalon 50-S) | | 3.00 | 0.30 | |
| 5. DAP - Diammoium Phosphate - Reagent Grade - 98% | | 40.89 | 4.09 | |
| TOTALS | | 100.00% | 10.00 gms. | |

The 50% active herbicide powder was prepared in accordance with Example I. Water solubility and oven stability were, likewise, similar.

EXAMPLE IV

The following ingredients were dry blended:

| Ingredients | % Active Ingredients | Weight % Reagents | Makeup for Grinding of 15 Grams - In Grams | HPLC (High Performance Liquid Chromatography Analysis) |
|---|---|---|---|---|
| 1. Picloram acid Tech. Grade - (95%) | 50.00 | 52.63 | 7.89 | 49.18 |
| 2. Sodium napthalenesulfonate formaldehyde polymer (Lomar PW) | | 1.00 | 0.15 | |
| 3. Sorbitan tristearate (SPAN-65) | | 1.00 | 0.15 | |
| 4. Spray dry synthetic silica (Wessalon 50-S) | | 5.00 | 0.75 | |
| 5. TSP - Trisodium Phosphate - (Anhyd) | | 40.37 | 6.06 | |
| TOTALS | | 100.00% | 15.00 gms. | |

The 50% active herbicide powder was prepared in accordance with Example I. Water solubility and oven stability were, likewise, similar.

EXAMPLE V

The following ingredients were dry blended:

| Ingredients | % Active Ingredients | Weight % Reagents | Makeup for Grinding of 15 Grams - In Grams | HPLC (High Performance Liquid Chromatography Analysis) |
|---|---|---|---|---|
| 1. Quinclorac acid Tech. Grade - (94%) | 25.00 | 26.60 | 3.99 | 24.85 |
| 2. Sodium napthalenesulfonate formaldehyde polymer (Lomar PW) | | 1.00 | 0.15 | |
| 3. Sorbitan tristearate (SPAN-65) | | 1.00 | 0.15 | |
| 4. Spray dry synthetic silica (Wessalon 50-S) | | 5.00 | 0.75 | |
| 5. TSP - Trisodium Phosphate - (Anhyd) | | 66.40 | 9.96 | |
| TOTALS | | 100.00% | 15.00 gms. | |

Ingredients 1-5 of Example V were ground to a fine, dry powder (averaging about 50 microns particle size) in a laboratory analytical mill. The mixture was transferred to a capped glass container. A 2 gm. sample of the 50% active herbicide powder prepared in accordance with Example V was added to a glass graduated cylinder which contained 98 ml. of city water. The stoppered cylinder was inverted several times over a period of 5 minutes. The 2 weight percent of herbicidal agent added to the water dissolved, with only a small quantity of silica remaining as a dispersion. After 96 hours in an oven at 50° C., a sample of the powder indicated no visible changes.

EXAMPLE VI

The following ingredients were dry blended:

| Ingredients | % Active Ingredients | Weight % Reagents | Makeup for Grinding of 15 Grams - In Grams | HPLC (High Performance Liquid Chromatography Analysis) |
|---|---|---|---|---|
| Bentazon acid Tech. Grade - (94%) | 33.33 | 35.46 | 5.32 | 33.96 |
| 1. Acifluorfen acid Tech.Grade - (92%) | 16.67 | 18.12 | 2.72 | 16.66 |
| 2. Sodium napthalenesulfonate formaldehyde polymer (Lomar PW) | | 1.00 | 0.15 | |
| 3. Sorbitan tristearate (SPAN-65) | | 1.00 | 0.15 | |
| 4. Spray dry synthetic silica (Wessalon 50-S) | | 5.00 | 0.75 | |
| 5. DAP - Diammonium Phosphate - Reagent Grade - 98% | | 39.42 | 5.91 | |
| TOTALS | | 100.00% | 15.00 gms. | |

Ingredients 1-6 of Example VI were ground to a fine, dry powder (averaging about 50 microns particle size) in a laboratory analytical mill. The mixture was transferred to a capped glass container. A 2 gm. sample of the 50% active herbicide powder prepared in accordance with Example VI was added to a glass graduated cylinder which contained 98 ml. of city water. The stoppered cylinder was inverted several times over a period of 5 minutes. The 2 weight percent of herbicidal agent added to the water dissolved, with only a small quantity of silica remaining as a dispersion. After 96 hours in an oven at 50° C., a sample of the powder indicated no visible changes.

EXAMPLE VII

The following ingredients were dry blended:

| Ingredients | % Active Ingredients | Weight % Reagents | Makeup for Grinding of 15 Grams - In Grams | HPLC (High Performance Liquid Chromatography Analysis) |
|---|---|---|---|---|
| 1. Triclopyr acid Tech. Grade - (98%) | 16.67 | 17.01 | 2.55 | 17.25 |
| 2. 2,4-D acid Tech.Grade - (97%) | 33.33 | 34.36 | 5.15 | 33.87 |
| 3. Sodium napthalenesulfonate formaldehyde polymer (Lomar PW) | | 1.00 | 0.15 | |
| 4. Sorbitan tristearate (SPAN-65) | | 1.00 | 0.15 | |
| 5. Spray dry synthetic silica (Wessalon 50-S) | | 5.00 | 0.75 | |
| 6. DAP - Diammonium Phosphate - Reagent Grade - 98% | | 41.63 | 6.25 | |
| TOTALS | | 100.00% | 15.00 gms. | |

Ingredients 1-6 of Example VII were ground to a fine, dry powder (averaging about 50 microns particle size) in a laboratory analytical mill. The mixture was transferred to a capped glass container. A 2 gm. sample of the 50% active herbicide powder prepared in accordance with Example VII was added to a glass graduated cylinder which contained 98 ml. of city water. The stoppered cylinder was inverted several times over a period of 5 minutes. The 2 weight percent of herbicidal agent added to the water dissolved, with only a small quantity of silica remaining as a dispersion. After 96 hours in an oven at 50° C., a sample of the powder indicated no visible changes.

EXAMPLE VIII

The following ingredients were dry blended:

| Ingredients | % Active Ingredients | Weight % Reagents | Makeup for Grinding of 15 Grams - In Grams | HPLC (High Performance Liquid Chromatography Analysis) |
|---|---|---|---|---|
| 1. Picloram acid Tech. Grade - (95%) | 10.00 | 10.53 | 1.58 | 10.08 |
| 2. 2,4-D acid Tech.Grade - (97%) | 40.00 | 41.24 | 6.19 | 40.27 |
| 3. Sodium napthalenesulfonate formaldehyde polymer (Lomar PW) | | 1.00 | 0.15 | |
| 4. Sorbitan tristearate (SPAN-65) | | 1.00 | 0.15 | |
| 5. Spray dry synthetic silica (Wessalon 50-S) | | 5.00 | 0.75 | |
| 6. TSP - Trisodium Phosphate - (Anhyd) | | 41.23 | 6.18 | |
| TOTALS | | 100.00% | 15.00 gms. | |

The 50% active herbicide powder was prepared in accordance with Example VII. Water solubility and oven stability were, likewise, similar.

EXAMPLE IX

The following ingredients were dry blended:

| Ingredients | % Active Ingredients | Weight % Reagents | Makeup for Grinding of 15 Grams - In Grams | HPLC (High Performance Liquid Chromatography Analysis) |
|---|---|---|---|---|
| 1. Clopyralid acid Tech. Grade - (95%) | 8.00 | 8.42 | 1.26 | 8.09 |
| 2. 2,4-D acid Tech.Grade - (97%) | 42.00 | 43.30 | 6.50 | 41.81 |
| 3. Sodium napthalenesulfonate formaldehyde polymer (Lomar PW) | | 1.00 | 0.15 | |
| 4. Sorbitan tristearate (SPAN-65) | | 1.00 | 0.15 | |
| 5. Spray dry synthetic silica (Wessalon 50-S) | | 5.00 | 0.75 | |
| 6. DSP - Disodium Phosphate - (Anhyd) | | 41.28 | 6.19 | |
| TOTALS | | 100.00% | 15.00 gms. | |

The 50% active herbicide powder was prepared in accordance with Example VII. Water solubility and oven stability were, likewise, similar.

EXAMPLE X

The following ingredients were dry blended:

| Ingredients | % Active Ingredients | Weight % Reagents | Makeup for Grinding of 15 Grams - In Grams | HPLC (High Performance Liquid Chromatography Analysis) |
|---|---|---|---|---|
| 1. Quinclorac acid Tech. Grade - (94%) | 13.33 | 14.18 | 2.13 | 14.35 |
| 2. Dichlorprop acid Tech.Grade - (94%) | 26.67 | 28.37 | 4.26 | 27.28 |
| 3. Sodium napthalenesulfonate formaldehyde polymer (Lomar PW) | | 1.00 | 0.15 | |
| 4. Sorbitan tristearate (SPAN-65) | | 1.00 | 0.15 | |
| 5. Spray dry synthetic silica (Wessalon 50-S) | | 5.00 | 0.75 | |
| 6. TSP - Trisodium Phosphate - (Anhyd) | | 50.45 | 7.56 | |
| TOTALS | | 100.00% | 15.00 | |

-continued

| Ingredients | % Active Ingredients | Weight % Reagents | Makeup for Grinding of 15 Grams - In Grams | HPLC (High Performance Liquid Chromatography Analysis) gms. |
|---|---|---|---|---|

Ingredients 1-6 of Example X were ground to a fine, dry powder (averaging about 50 microns particle size) in a laboratory analytical mill. The mixture was transferred to a capped glass container. A 2 gm. sample of the 50% active herbicide powder prepared in accordance with Example X was added to a glass graduated cylinder which contained 98 ml. of city water. The stoppered cylinder was inverted several times over a period of 5 minutes. The 2 weight percent of herbicidal agent added to the water dissolved, with only a small quantity of silica remaining as a dispersion. After 96 hours in an oven at 50° C., a sample of the powder indicated no visible changes.

EXAMPLE XI

The following ingredients were dry blended:

| Ingredients | % Active Ingredients | Weight % Reagents | Makeup for Grinding of 15 Grams - In Grams | HPLC (High Performance Liquid Chromatography Analysis) |
|---|---|---|---|---|
| 1. 2.4-D acid Tech. Grade - (97%) | 31.25 | 32.22 | 4.83 | 30.66 |
| 2. MCPP acid Tech.Grade - (Dry, 95%) | 15.62 | 16.44 | 2.47 | 15.76 |
| 3. Clopyralid Acid - Tech. Grade - (95%) | 3.13 | 3.29 | 0.49 | 3.36 |
| 4. Sodium napthalenesulfonate formaldehyde polymer (Lomar PW) | | 1.00 | 0.15 | |
| 5. Sorbitan tristearate (SPAN-65) | | 1.00 | 0.15 | |
| 6. Spray dry synthetic silica (Wessalon 50-S) | | 5.00 | 0.75 | |
| 7. DAP - Diammonium Phosphate - Reagent Grade - 98% | | 41.05 | 6.16 | |
| TOTALS | | 100.00% | 15.00 gms. | |

Ingredients 1-7 of Example XI were ground to a fine, dry powder (averaging about 50 microns particle size) in a laboratory analytical mill. The mixture was transferred to a capped glass container. A 2 gm. sample of the 50% active herbicide powder prepared in accordance with Example XI was added to a glass graduated cylinder which contained 98 ml. of city water. The stoppered cylinder was inverted several times over a period of 5 minutes. The 2 weight percent of herbicidal agent added to the water dissolved, with only a small quantity of silica remaining as a dispersion. After 96 hours in an oven at 50° C., a sample of the powder indicated no visible changes.

EXAMPLE XII

The following ingredients were dry blended:

| Ingredients | % Active Ingredients | Weight % Reagents | Makeup for Grinding of 15 Grams - In Grams | HPLC (High Performance Liquid Chromatography Analysis) |
|---|---|---|---|---|
| 1. 2.4-D acid Tech. Grade - (97%) | 31.25 | 32.22 | 4.83 | 31.48 |
| 2. MCPP acid Tech.Grade - (Dry, 95%) | 15.62 | 16.44 | 2.47 | 15.83 |
| 3. Triclopyr Acid - Tech. Grade - (98%) | 3.13 | 3.19 | 0.48 | 3.13 |
| 4. Sodium napthalenesulfonate formaldehyde polymer (Lomar PW) | | 1.00 | 0.15 | |
| 5. Sorbitan tristearate (SPAN-65) | | 1.00 | 0.15 | |
| 6. Spray dry synthetic silica (Wessalon 50-S) | | 5.00 | 0.75 | |
| 7. DAP - Diammonium Phosphate - Reagent Grade - 98% | | 41.15 | 6.17 | |
| TOTALS | | 100.00% | 15.00 gms. | |

The 50% active herbicide powder was prepared in accordance with Example XI. Water solubility and oven stability were, likewise, similar.

EXAMPLE XIII

The following ingredients were dry blended:

| Ingredients | % Active Ingredients | Weight % Reagents | Makeup for Grinding of 15 Grams - In Grams | HPLC (High Performance Liquid Chromatography Analysis) |
|---|---|---|---|---|
| 1. 2.4-D acid Tech. Grade - (97%) | 31.25 | 32.22 | 4.83 | 32.07 |
| 2. MCPP acid Tech.Grade - (Dry, 95%) | 15.16 | 16.44 | 2.47 | 15.72 |
| 3. Picloram Acid - Tech. Grade - (95%) | 3.13 | 3.29 | 0.49 | 3.25 |
| 4. Sodium napthalenesulfonate formaldehyde polymer (Lomar PW) | | 1.00 | 0.15 | |
| 5. Sorbitan tristearate (SPAN-65) | | 1.00 | 0.15 | |
| 6. Spray dry synthetic silica (Wessalon 50-S) | | 5.00 | 0.75 | |
| 7. DAP - Diammonium Phosphate - Reagent Grade - 98% | | 41.05 | 6.16 | |
| TOTALS | | 100.00% | 15.00 gms. | |

The 50% active herbicide powder was prepared in accordance with Example XI. Water solubility and oven stability were, likewise, similar.

EXAMPLE XIV

The following ingredients were dry blended:

| Ingredients | % Active Ingredients | Weight % Reagents | Makeup for Grinding of 15 Grams - In Grams | HPLC (High Performance Liquid Chromatography Analysis) |
|---|---|---|---|---|
| 1. MCPA acid Tech. Grade - (95%) | 33.34 | 35.09 | 5.26 | 33.47 |
| 2. MCPP acid Tech.Grade - (Dry, 95%) | 13.33 | 14.03 | 2.10 | 13.13 |
| 3. Triclopyr Acid - Tech. Grade - (98%) | 3.33 | 3.40 | 0.51 | 3.00 |
| 4. Sodium napthalenesulfonate formaldehyde polymer (Lomar PW) | | 1.00 | 0.15 | |
| 5. Sorbitan tristearate (SPAN-65) | | 1.00 | 0.15 | |
| 6. Spray dry synthetic silica (Wessalon 50-S) | | 5.00 | 0.75 | |
| 7. TPP-Tripotassium Phosphate - (Anhyd) | | 40.48 | 6.08 | |
| TOTALS | | 100.00% | 15.00 gms. | |

Ingredients 1-7 of Example XIV were ground to a fine, dry powder (averaging about 50 microns particle size) in a laboratory analytical mill. The mixture was transferred to a capped glass container. A 2 gm. sample of the 50% active herbicide powder prepared in accordance with Example XIV was added to a glass graduated cylinder which contained 98 ml. of city water. The stoppered cylinder was inverted several times over a period of 5 minutes. The 2 weight percent of herbicidal agent added to the water dissolved, with only a small quantity of silica remaining as a dispersion. After 96 hours in an oven at 50° C., a sample of the powder indicated no visible changes.

EXAMPLE XV

The following ingredients were dry blended:

| Ingredients | % Active Ingredients | Weight % Reagents | Makeup for Grinding of 15 Grams - In Grams | HPLC (High Performance Liquid Chromatography Analysis) |
|---|---|---|---|---|
| 1. 2,4-D acid Tech. Grade - (97%) | 22.23 | 22.92 | 3.44 | 22.37 |
| 2. Dichlorprop acid Tech.Grade - (95%) | 22.22 | 23.39 | 3.51 | 23.53 |
| 3. Triclopyr Acid - Tech. Grade - (98%) | 5.55 | 5.66 | 0.85 | 4.93 |
| 4. Sodium napthalenesulfonate formaldehyde polymer (Lomar PW) | | 1.00 | 0.15 | |
| 5. Sorbitan tristearate (SPAN-65) | | 1.00 | 0.15 | |
| 6. Spray dry synthetic silica (Wessalon 50-S) | | 5.00 | 0.75 | |
| 7. DPP - Dipotassium Phosphate - (Anhyd) | | 41.03 | 6.15 | |
| TOTALS | | 100.00% | 15.00 gms. | |

Ingredients 1-7 of Example XV were ground to a fine, dry powder (averaging about 50 microns particle size) in a laboratory analytical mill. The mixture was transferred to a capped glass container. A 2 gm. sample of the 50% active herbicide powder prepared in accordance with Example XIV was added to a glass graduated cylinder which contained 98 ml. of city water. The stoppered cylinder was inverted several times over a period of 5 minutes. The 2 weight percent of herbicidal agent added to the water dissolved, with only a small quantity of silica remaining as a dispersion. After 96 hours in an oven at 50° C., a sample of the powder indicated no visible changes.

EXAMPLE XVI

The following ingredients were dry blended:

| Ingredients | % Active Ingredients | Weight % Reagents | Makeup for Grinding of 15 Grams - In Grams | HPLC (High Performance Liquid Chromatography Analysis) |
|---|---|---|---|---|
| 1. Bromoxynil Tech. Grade-96.9% | 35.00 | 36.12 | 7.22 | 35.77 |
| 2. Sodium napthalenesulfonate formaldehyde polymer (Lomar PW) | | 1.00 | 0.20 | |
| 3. Sorbitan tristearate (SPAN-65) | | 1.00 | 0.20 | |
| 4. Spray dry synthetic silica (Wessalon 50-S) | | 5.00 | 1.00 | |
| 5. TPP-Tripotassium phosphate (Anhyd) | | 56.88 | 11.38 | |
| TOTALS | | 100.00% | 20.00 gms. | |

Ingredients 1-5 of Example XVI were ground to a fine, dry powder (averaging about 50 microns particle size) in a laboratory analytical mill. The mixture was transferred to a capped glass container. A 2 gm. sample of the 35% active herbicide powder prepared in accordance with Example XVI was added to a glass graduated cylinder which contained 98 ml. of city water. The stoppered cylinder was inverted several times over a period of 5 minutes. The 2 weight percent of herbicidal agent added to the water dissolved, with only a small quantity of silica remaining as a dispersion. After 96 hours in an oven at 50° C., a sample of the powder indicated no visible changes.

EXAMPLE XVII

The following ingredients were dry blended:

| Ingredients | % Active Ingredients | Weight % Reagents | Makeup for Grinding of 15 Grams - In Grams | HPLC (High Performance Liquid Chromatography Analysis) |
|---|---|---|---|---|
| 1. Bromoxynil Tech. Grade-96.9% | 30.00 | 30.96 | 6.19 | 30.75 |
| 2. Sodium napthalenesulfonate formaldehyde polymer (Lomar PW) | | 1.00 | 0.20 | |
| 3. Sorbitan tristearate (SPAN-65) | | 1.00 | 0.20 | |
| 4. Spray dry synthetic | | 5.00 | 1.00 | |

| Ingredients | % Active Ingredients | Weight % Reagents | Makeup for Grinding of 15 Grams - In Grams | HPLC (High Performance Liquid Chromatography Analysis) |
|---|---|---|---|---|
| silica (Wessalon 50-S) | | | | |
| 5. DSP-Disodium phosphate (Anhyd) | | 62.04 | 12.41 | |
| TOTALS | | 100.00% | 20.00 gms. | |

The 30% active herbicide powder was prepared in accordance with Example XVI. Water solubility and oven stability were, likewise, similar.

EXAMPLE XVIII

The following ingredients were dry blended:

| Ingredients | % Active Ingredients | Weight % Reagents | Makeup for Grinding of 15 Grams - In Grams | HPLC (High Performance Liquid Chromatography Analysis) |
|---|---|---|---|---|
| 1. Bromoxynil Tech. Grade-96.9% | 25.00 | 25.80 | 5.16 | 25.00 |
| 2. Sodium napthalenesulfonate formaldehyde polymer (Lomar PW) | | 1.00 | 0.20 | |
| 3. Sorbitan tristearate (SPAN-65) | | 1.00 | 0.20 | |
| 4. Spray dry synthetic silica (Wessalon 50-S) | | 5.00 | 1.00 | |
| 5. TSP-Trisodium phosphate (Anhyd) | | 67.20 | 13.44 | |
| TOTALS | | 100.00% | 20.00 gms. | |

The 25% active herbicide powder was prepared in accordance with Example XVI. Water solubility and oven stability were, likewise, similar.

EXAMPLE XIX

The following ingredients were dry blended:

| Ingredients | % Active Ingredients | Weight % Reagents | Makeup for Grinding of 15 Grams - In Grams | HPLC (High Performance Liquid Chromatography Analysis) |
|---|---|---|---|---|
| 1. Ioxynil Tech. Grade-97% | 40.00 | 41.24 | 6.19 | 39.30 |
| 2. Sodium napthalenesulfonate formaldehyde polymer (Lomar PW) | | 1.00 | 0.15 | |
| 3. Sorbitan tristearate (SPAN-65) | | 1.00 | 0.15 | |
| 4. Spray dry synthetic silica (Wessalon 50-S) | | 2.00 | 0.30 | |
| 5. TSP-Trisodium phosphate (Anhyd) | | 54.76 | 8.21 | |
| TOTALS | | 100.00% | 15.00 gms. | |

Ingredients 1-5 of Example XIX were ground to a fine, dry powder (averaging about 50 microns particle size) in a laboratory analytical mill. The mixture was transferred to a capped glass container. A 2 gm. sample of the 40% active herbicide powder prepared in accordance with Example XIV was added to a glass graduated cylinder which contained 98 ml. of city water. The stoppered cylinder was inverted several times over a period of 5 minutes. The 2 weight percent of herbicidal agent added to the water dissolved, with only a small quantity of silica remaining as a dispersion. After 96 hours in an oven at 50° C., a sample of the powder indicated no visible changes.

EXAMPLE XX

The following ingredients were dry blended:

| Ingredients | % Active Ingredients | Weight % Reagents | Makeup for Grinding of 15 Grams - In Grams | HPLC (High Performance Liquid Chromatography Analysis) |
|---|---|---|---|---|
| 1. Ioxynil Tech. Grade-97% | 35.00 | 36.08 | 5.41 | 34.00 |
| 2. Sodium napthalenesulfonate formaldehyde polymer (Lomar PW) | | 1.00 | 0.15 | |
| 3. Sorbitan tristearate (SPAN-65) | | 1.00 | 0.15 | |
| 4. Spray dry synthetic silica (Wessalon 50-S) | | 2.00 | 0.30 | |
| 5. DPP-Dipotassium phosphate (Anhyd) | | 59.92 | 8.99 | |
| TOTALS | | 100.00% | 15.00 gms. | |

The 35% active herbicide powder was prepared in accordance with Example XIX. Water solubility and oven stability were, likewise, similar.

EXAMPLE XXI

The following ingredients were dry blended:

| Ingredients | % Active Ingredients | Weight % Reagents | Makeup for Grinding of 15 Grams - In Grams | HPLC (High Performance Liquid Chromatography Analysis) |
|---|---|---|---|---|
| 1. Ioxynil Tech. Grade-97% | 25.00 | 25.77 | 3.87 | 25.00 |
| 2. Sodium napthalenesulfonate formaldehyde polymer (Lomar PW) | | 1.00 | 0.15 | |

-continued

| Ingredients | % Active Ingredients | Weight % Reagents | Makeup for Grinding of 15 Grams - In Grams | HPLC (High Performance Liquid Chromatography Analysis) |
|---|---|---|---|---|
| 3. Sorbitan tristearate (SPAN-65) | | 1.00 | 0.15 | |
| 4. Spray dry synthetic silica (Wessalon 50-S) | | 2.00 | 0.30 | |
| 5. DAP-Diammonium phosphate- Reagent Grade - 98% | | 70.23 | 10.53 | |
| TOTALS | | 100.00% | 15.00 gms. | |

The 25% active herbicide powder was prepared in accordance with Example XIX. Water solubility and oven stability were, likewise, similar.

The prepared aqueous sample containing 2.0 weight percent of the 25% to 50% active herbicide powder in all instances yielded a substantially clear solution within two minutes. It was not necessary to heat or agitate the product to maintain the ingredients in solution while sitting on a shelf for several days at room temperature. Tests of the dry blended material dissolved in water yielded clear solutions at levels of 0.5%, 1%, 2%, and 4 weight percent. Weight percent in this respect means 1 gram of the active dry powder for each 99 milliliters of tap water. Normal herbicide application concentrations range from about ½ weight percent of the active acid to about 2% of the active acid.

EXAMPLE XXII

The following ingredients were dry blended:

| Ingredients | % Active Ingredients | Weight % Reagents | Makeup for Grinding of 15 Grams - In Grams | HPLC (High Performance Liquid Chromatography Analysis) |
|---|---|---|---|---|
| 1. MCPA acid Tech. Grade-(94%) | 20.00 | 21.28 | 4.26 | 20.75 |
| 2. Bromoxynil Tech. Grade-(96.9%) | 20.00 | 20.64 | 4.13 | 20.33 |
| 2. Sodium napthalenesulfonate formaldehyde polymer (Lomar PW) | | 1.00 | 0.20 | |
| 3. Sorbitan tristearate (SPAN-65) | | 1.00 | 0.20 | |
| 4. Spray dry synthetic silica (Wessalon 50-S) | | 5.00 | 1.00 | |
| 5. TSP-Trisodium phosphate (Anhyd) | | 51.08 | 10.21 | |
| TOTALS | | 100.00% | 20.00 gms. | |

Ingredients 1-6 of Example XXII were ground to a fine, dry powder (averaging about 50 microns particle size) in a laboratory analytical mill. The mixture was transferred to a capped glass container. A 2 gm. sample of the 40% active herbicide powder prepared in accordance with Example XXII was added to a glass graduated cylinder which contained 98 ml. of city water. The stoppered cylinder was inverted several times over a period of 5 minutes. The 2 weight percent of herbicidal agent added to the water dissolved, with only a small quantity of silica remaining as a dispersion. After 96 hours in an oven at 50° C., a sample of the powder indicated no visible changes.

It has been determined that the best results are obtained when an anhydrous DAP, DPP and DSP are utilized as the solubilization medium for the substituted phenoxy and/or benzoic acid herbicidal agent, with the preferred medium being DAP. In all cases, the anhydrous DAP, DPP, DSP, TSP or TPP solubilization medium should contain less than about 1% water by weight.

We claim:

1. A dry, water-soluble herbicide powder composition consisting essentially of:
    a dry blended admixture of
        a first quantity of dry, powder particles of a substantially solid herbicidal agent selected from the group consisting of a herbicidally active substituted heterocyclic acid, a herbicidally active substituted heterocyclic acid combined with a solid herbicidally active substituted phenoxy acid, a herbicidally active substituted heterocyclic acid combined with a solid herbicidally active substituted benzoic acid, a herbicidally active substituted heterocyclic acid combined with a herbicidally active substituted phenoxy acid and a herbicidally active substituted benzoic acid, a herbicidally active substituted phenol, a herbicidally active phenol combined with a herbicidally active substituted heterocyclic acid, a herbicidally active phenol combined with a herbicidally active substituted phenoxy acid, and a herbicidally active phenol combined with a herbicidally active substituted benzoic acid, each of which alone, or in combination with one another, are not readily soluble in water, and
        a second quantity of dry, solid, powder particles selected from the group consisting of diammonium phosphate, dipotassium phosphate, disodium phosphate, trisodium phosphate, tripotassium phosphate, and mixtures thereof as a solubilization medium for the herbicidal agent,
    said first and second quantities of the herbicidal agent and the solubilization medium being the predominate constituents of the composition,
    there being at least about 1 mole of solubilization medium for each mole of herbicidal agent,
    said herbicidal agent and the solubilization medium having been dry blended in powdered form without changing the physical state of the particles to retain the discrete particulate character of each of said first and second quantities of said particles, and in the absence of chemical reaction between said herbicidal agent and said solubilization medium to form a relatively uniform dry mixture thereof,
    there being a sufficient quantity of the phosphate medium in the dry blended mixture in relationship to the quantity of herbicidal agent combined therewith such that the dry blended powder mixture will dissolve in water during preparation of a herbicidal solution therefrom that contains an adequate proportion of the herbicidal agent to provide from about 0.1 to about 2-½% by weight of the active herbicidal agent in the herbicidal solution.

2. A herbicide as set forth in claim 1 wherein said dry solubilization medium is diammonium phosphate.

3. A herbicide as set forth in claim 1 wherein said dry solubilization medium is dipotassium phosphate.

4. A herbicide as set forth in claim 1 wherein said dry solubilization medium is trisodium phosphate.

5. A herbicide as set forth in claim 1 wherein said dry, solid, powder herbicide is 3,6-dichloropicolinic acid.

6. A herbicide as set forth in claim 1 wherein said dry, solid, powder herbicide is 3,5,6-trichloro-2-pyridyloxyacetic acid.

7. A herbicide as set forth in claim 1 wherein said dry, solid, powder herbicide is 4-amino-3,5,6-trichloropicolinic acid.

8. A herbicide as set forth in claim 1 wherein said dry, solid, powder herbicide is 3,7-dichloro-8-quinolinecarboxylic acid.

9. A herbicide as set forth in claim 1 wherein solid, powder herbicide is 3-isopropyl-1H-2,1,3-benzothiadiazin-4(3H)-one 2,2-dioxide.

10. A herbicide as set forth in claim 1 wherein said dry, solid, powder herbicide is 3,5-dibromo-4-hydroxybenzonitrile.

11. A herbicide as set forth in claim 1 wherein said dry, solid, powder herbicide is 3,5-dibromo-4-hydroxybenzonitrile and 2-methyl-chlorophenoxyacetic acid.

12. A herbicide as set forth in claim 1 wherein said dry, solid, powder herbicide is 3,5-diiodo-4-hydroxybenzonitrile.

13. A herbicide as set forth in claim 1 wherein said dry, solid, powder herbicide is 3,5-diiodo-4-hydroxybenzonitrile and 3,5-dibromo-4-hydroxybenzonitrile.

14. A herbicide as set forth in claim 1 wherein said dry, solid, powder herbicide is a herbicide as set forth in any one of claims 5, 6, 7, 8, 9, 10, 11, 12 or 13 and further including a substituted phenoxy acid herbicide.

15. A herbicide as set forth in claim 1 wherein said dry, solid, powder herbicide is a herbicide as set forth in any one of claims 5, 6, 7, 8, 9, 10, 11, 12 or 13 and further including a substituted benzoic acid herbicide.

16. A herbicide as set forth in claim 14 wherein the dry blended admixture includes a mixture of substituted phenoxy acid and substituted benzoic acid herbicides.

17. A method of preparing a dry, water-soluble, herbicide powder composition consisting essentially of the steps of:

providing a first quantity of dry, powder particles of a substantially solid herbicidal agent selected from the group consisting of a herbicidally active substituted heterocyclic acid, a herbicidally active substituted heterocyclic acid combined with a solid herbicidally active substituted phenoxy acid, a herbicidally active substituted heterocyclic acid combined with a solid herbicidally active substituted benzoic acid, a herbicidally active substituted heterocyclic acid combined with a herbicidally active substituted phenoxy acid and a herbicidally active substituted benzoic acid, and a herbicidally active substituted phenol, a herbicidally active phenol combined with a herbicidally active substituted heterocyclic acid, a herbicidally active phenol combined with a herbicidally active substituted phenoxy acid, and a herbicidally active phenol combined with a herbicidally active substituted benzoic acid, each of which alone, or in combination with one another, are not readily soluble in water, providing a second quantity of dry, solid powder particles consisting essentially of a solubilization medium for the herbicidal agent and selected from the group consisting of diammonium phosphate, dipotassium phosphate, disodium phosphate, trisodium phosphate and tripotassium phosphate, said first and second quantities of the herbicidal agent and the solubilization medium being the predominate constituents of the composition, there being at least 1 mole of solubilization medium for each mole of herbicidal agent; and dry blending the herbicidal agent and the solubilization medium in powdered form without changing the physical state of the particles to retain the discrete particulate character of each of said first and second quantities of said particles, and in the absence of chemical reaction between said herbicidal agent and said solubilization medium to produce a relatively uniform dry mixture thereof, a sufficient quantity of the phosphate solubilization medium being provided in the dry blended mixture in relationship to the quantity of herbicidal agent combined therewith to cause the powdered dry blended mixture to substantially dissolve in water during preparation by the applicator of a herbicidal solution which contains an adequate proportion of the herbicidal agent to provide from about 0.1% to about 2-$\frac{1}{2}$% by weight of the active herbicidal agent in the herbicidal solution.

18. A method as set forth in claim 17 wherein a sufficient quantity of the phosphate medium is present in the dry blended mixture to provide at least about 1 to about 5 mols of the medium for each mol of active herbicidal agent in the dry blended mixture.

19. A method as set forth in claim 17 wherein is included the step of providing a mixture of said herbicidally active agents for dry blending with the phosphate medium.

20. A method as set forth in claim 17 wherein said dry solubilization medium is diammonium phosphate.

21. A method as set forth in claim 17 wherein said dry solubilization medium is dipotassium phosphate.

22. A method as set forth in claim 17 wherein said dry solubilization medium is trisodium phosphate.

23. A method as set forth in claim 17 wherein said dry, solid, powder herbicide is 3,6-dichloropicolinic acid.

24. A method as set forth in claim 17 wherein said dry, solid, powder herbicide is 3,5,6-trichloro-2-pyridyloxyacetic acid.

25. A method as set forth in claim 17 wherein said dry, solid, powder herbicide is 4-amino-3,5,6-trichloropicolinic acid.

26. A method as set forth in claim 17 wherein said dry, solid, powder herbicide is 3,7-dichloro-8-quinolinecarboxylic acid.

27. A method as set forth in claim 17 wherein said dry, solid, powder herbicide is 3-isopropyl-1H-2,1,3-benzothiadiazin-4(3H)-one 2,2-dioxide.

28. A method as set forth in claim 17 wherein said dry, solid, powder herbicide is 3,5-dibromo-4-hydroxybenzonitrile.

29. A method as set forth in claim 17 wherein said dry, solid, powder herbicide is 3,5-dibromo-4-hydroxybenzonitrile and 2-methyl-chlorophenoxyacetic acid.

30. A method as set forth in claim 17 wherein said dry, solid, powder herbicide is 3,5-diiodo-4-hydroxybenzonitrile.

31. A method as set forth in claim 17 wherein said dry, solid, powder herbicide is 3,5-diiodo-4-hydroxybenzonitrile and 3,5-dibromo-4-hydroxybenzonitrile.

32. A method as set forth in claim 17 wherein said dry, solid, powder herbicide is a herbicide as set forth in any one of claims 23, 24, 25, 26, 27, 28, 29, 30 or 31 and further including a substituted phenoxy acid herbicide.

33. A method as set forth in claim 17 wherein said dry, solid, powder herbicide is a herbicide as set forth in any one of claims 23, 24, 25, 26, 27, 28, 29, 30 or 31 and further including a substituted benzoic acid herbicide.

34. A method as set forth in claim 32 wherein the dry blended admixture includes a mixture of substituted phenoxy acid and substituted benzoic acid herbicides.

35. A method as set forth in claim 17 wherein is included the step of incorporating an anti-caking agent in the dry blended mixture.

36. A method of preparing a herbicide solution consisting essentially of the steps of:

adding to a volume of water, a dry powdered herbicidal composition containing a first quantity of dry, powder particles of a substantially solid herbicidal agent selected from the group consisting of a herbicidally active substituted heterocyclic acid, a herbicidally active substituted heterocyclic acid combined with a solid herbicidally active substituted phenoxy acid, a herbicidally active substituted heterocyclic acid combined with a solid herbicidally active substituted benzoic acid, a herbicidally active substituted heterocyclic acid combined with a herbicidally active substituted phenoxy acid and a herbicidally active substituted benzoic acid, a herbicidally active substituted phenol, a herbicidally active phenol combined with a herbicidally active substituted heterocyclic acid, a herbicidally active phenol combined with a herbicidally active substituted phenoxy acid, and a herbicidally active phenol combined with a herbicidally active substituted benzoic acid, each of which alone, or in combination with one another, are not readily soluble in water, and a second quantity of dry, solid, powder particles of a selected from the group consisting of diammonium phosphate, dipotassium phosphate, disodium phosphate, trisodium phosphate, tripotassium phosphate, and mixtures thereof as a solubilization medium for the herbicidal agent, said first and second quantities of the herbicidal agent and the solubilization medium being the predominate constituents of the composition, there being at least about 1 mole of solubilization medium for each mole of herbicidal agent, said herbicidal agent and the solubilization medium having been subjected to only dry blended in powdered form without changing the physical state of the particles to retain the discrete particulate character of each of said first and second quantities of said particles, and in the absence of chemical reaction between said herbicidal agent and said solubilization medium, to form a relatively uniform dry mixture thereof;

adding a sufficient quantity of the powdered dry blended admixture of the herbicidal agent and the phosphate solubilization medium to the volume of water to cause the powdered dry blended mixture dissolved in the water to provide from about 0.1% to about 2-½% by weight of the active herbicidal agent in the herbicidal solution; and agitating the water containing the herbicidal agent and the solubilization medium for a time period sufficient to effect substantial dissolution of the agent and the medium in the volume of water.

* * * * *